(12) United States Patent
Auyoung et al.

(10) Patent No.: US 12,156,686 B2
(45) Date of Patent: *Dec. 3, 2024

(54) DEVICE FOR PERFORMING A SURGICAL PROCEDURE AND METHOD

(71) Applicant: MEDTRONIC HOLDING COMPANY SÀRL, Tolochenaz (CH)

(72) Inventors: Bryan J. Auyoung, Santa Clara, CA (US); Warren C. Sapida, Sunnyvale, CA (US)

(73) Assignee: Medtronic Holding Company SARL, Tolochenaz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/479,344

(22) Filed: Oct. 2, 2023

(65) Prior Publication Data

US 2024/0024009 A1    Jan. 25, 2024

Related U.S. Application Data

(60) Continuation of application No. 17/216,110, filed on Mar. 29, 2021, now Pat. No. 11,771,485, which is a division of application No. 15/650,026, filed on Jul. 14, 2017, now Pat. No. 10,959,765, which is a division of application No. 13/838,794, filed on Mar. 15, 2013, now Pat. No. 9,730,746.

(51) Int. Cl.
*A61B 17/88* (2006.01)
*A61M 25/10* (2013.01)

(52) U.S. Cl.
CPC ...... *A61B 17/8855* (2013.01); *A61B 17/8805* (2013.01); *A61B 17/8811* (2013.01); *A61B 17/885* (2013.01); *A61B 17/8852* (2013.01); *A61M 25/10* (2013.01)

(58) Field of Classification Search
CPC .................. A61B 17/8855; A61B 17/8858
See application file for complete search history.

(56) References Cited

U.S. PATENT DOCUMENTS

| | | | | |
|---|---|---|---|---|
| 4,261,339 A | * | 4/1981 | Hanson | A61M 60/295 604/914 |
| 4,483,340 A | * | 11/1984 | Fogarty | A61M 25/104 604/913 |
| 5,900,444 A | | 5/1999 | Zamore | |
| 6,110,192 A | | 8/2000 | Ravencroft et al. | |

(Continued)

*Primary Examiner* — Nicholas W Woodall
(74) *Attorney, Agent, or Firm* — Sorell, Lenna & Schmidt, LLP

(57) ABSTRACT

A medical balloon device includes an outer member extending along an axis. An inflatable member has a proximal end extending from a first end of the outer member and a distal end. An inner member is positioned within the outer member and the inflatable member such that a first end of the inner member is coupled to the distal end of the inflatable member. A support member is movably disposed within the inner member and includes a first end configured to removably engage the first end of the inner member. Translation of the support member along the axis causes the inflatable member to move between a first position in which the inflatable member has a first length and a first profile and a second position in which the inflatable member has a second reduced length and a second reduced profile. Methods of use are disclosed.

21 Claims, 10 Drawing Sheets

(56) References Cited

U.S. PATENT DOCUMENTS

| | | |
|---|---|---|
| 6,596,818 B1 | 7/2003 | Zamore |
| 6,656,550 B1 | 12/2003 | Zamore |
| 7,749,585 B2 | 7/2010 | Zamore |
| 7,771,447 B2 | 8/2010 | Kunis |
| 7,883,537 B2 | 2/2011 | Grayzel et al. |

* cited by examiner

DEVICE FOR PERFORMING A SURGICAL PROCEDURE AND METHOD

CROSS-REFERENCE TO RELATED APPLICATIONS

This application is a continuation of U.S. patent application Ser. No. 17/216,110, filed, Mar. 29, 2021, which is a divisional of application U.S. patent application Ser. No. 15/650,026, filed Jul. 14, 2017, which is a divisional of application U.S. patent application Ser. No. 13/838,794, filed on Mar. 15, 2013, now U.S. Pat. No. 9,730,746. These applications are hereby incorporated by reference herein, in their entireties.

TECHNICAL FIELD

The present disclosure generally relates to medical devices for the treatment of musculoskeletal structures, and more particularly to a surgical system and method employing an inflatable member having a reduced profile when in an unexpanded configuration to facilitate insertion of the inflatable member into a cannula and/or removal of the inflatable member from a cannula.

BACKGROUND

Height loss is commonly associated with spinal fractures, typically referred to as vertebral compression fractures. A large segment of osteoporotic patients experience vertebral compression fractures, with an estimated 700,000 such fractures occurring annually. Kyphoplasty is a minimally invasive procedure that is used to treat vertebral compression fractures using a combination of vertebroplasty utilizing bone cement with balloon catheter technology. The kyphoplasty procedure restores height of the collapsed spinal bone which diminishes associated back pain.

In a kyphoplasty procedure, an inflatable balloon tamp (IBT) is inserted inside a fractured vertebral body. The IBT is inflated to separate the vertebra and create a cavity that is filled with bone cement to maintain the height correction. In the alternative, ITBs may also be used in long bones, such as the femur, or other bones, such as the wrist or heel. Currently, in a kyphoplasty procedure, the IBT is typically stored or inserted in a cannula sized for the balloon with a diameter of the cannula of a sufficient width to accommodate the balloon in its entirety. Because the kyphoplasty requires an insertion into tissue, it is desirable to reduce the outer diameter of the cannula, while still allowing for insertion and removal of the IBT from the cannula. This disclosure describes an improvement over these prior art technologies.

SUMMARY

Accordingly, a surgical system and method for correction of a bone injury or disorder are provided. In one embodiment, in accordance with the principles of the present disclosure, the surgical system includes a device for performing a surgical procedure. The device comprises an outer member extending along an elongated axis and comprising an inner surface defining a first passageway. An inflatable member has a proximal end extending from a first end of the outer member and a distal end. The inflatable member includes an inner surface defining a chamber. An inner member is positioned within the first passageway and the chamber such that a first end of the inner member is coupled to the distal end of the inflatable member. The inner member has an inner surface defining a second passageway. A support member is movably disposed within the second passageway and includes a first end configured to removably engage the first end of the inner member. Translation of the support member along the elongated axis in a first direction causes the inflatable member to move between a first position in which the inflatable member has a first length and a first profile and a second position in which the inflatable member has a second length and a second reduced profile, the second length being greater than the first length.

In one embodiment, in accordance with the principles of the present disclosure, the surgical system includes a device comprising an outer member defining an axis and comprising an inner surface defining a passageway. An inflatable member has a first end extending from a first end of the outer member. The inflatable member includes an inner surface defining a chamber. A support member is movably disposed within the passageway and the chamber. The support member includes a first end that is coupled to a second end of the inflatable member. Translation of the support member along the elongated axis in a first direction causes the inflatable member to move between a first position in which the inflatable member has a first length and a first profile and a second position in which the inflatable member has a second length and a second reduced profile, the second length being greater than the first length. Rotation of the support member relative to the outer member about the axis causes the inflatable member to twist about the inner member such that the inflatable member moves between the second position and a third position in which the inflatable member has a third profile that is less than the second profile.

In one embodiment, in accordance with the principles of the present disclosure, a method for repairing a bone is provided. The method comprises the steps of: providing a device comprising an outer member defining an axis and comprising an inner surface defining a first passageway, an inflatable member having a first end extending from a first end of the outer member, the inflatable member including an inner surface defining a chamber, an inner member positioned within the first passageway and the chamber such that a first end of the inner member is coupled to a second end of the inflatable member, the inner member having an inner surface defining a second passageway, and a support member movably disposed within the second passageway; inflating the inflatable member such that the inflatable member has an inflated height; deflating the inflatable member such that the inflatable member is in a first position defined by a first height and a first length, the first height being less than the inflated height; and translating the support member along the axis in a first direction such that the inflatable member moves from the first position to a second position defined by a second height and a second length, the second height being less than the first height and the second length being greater than the first length.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
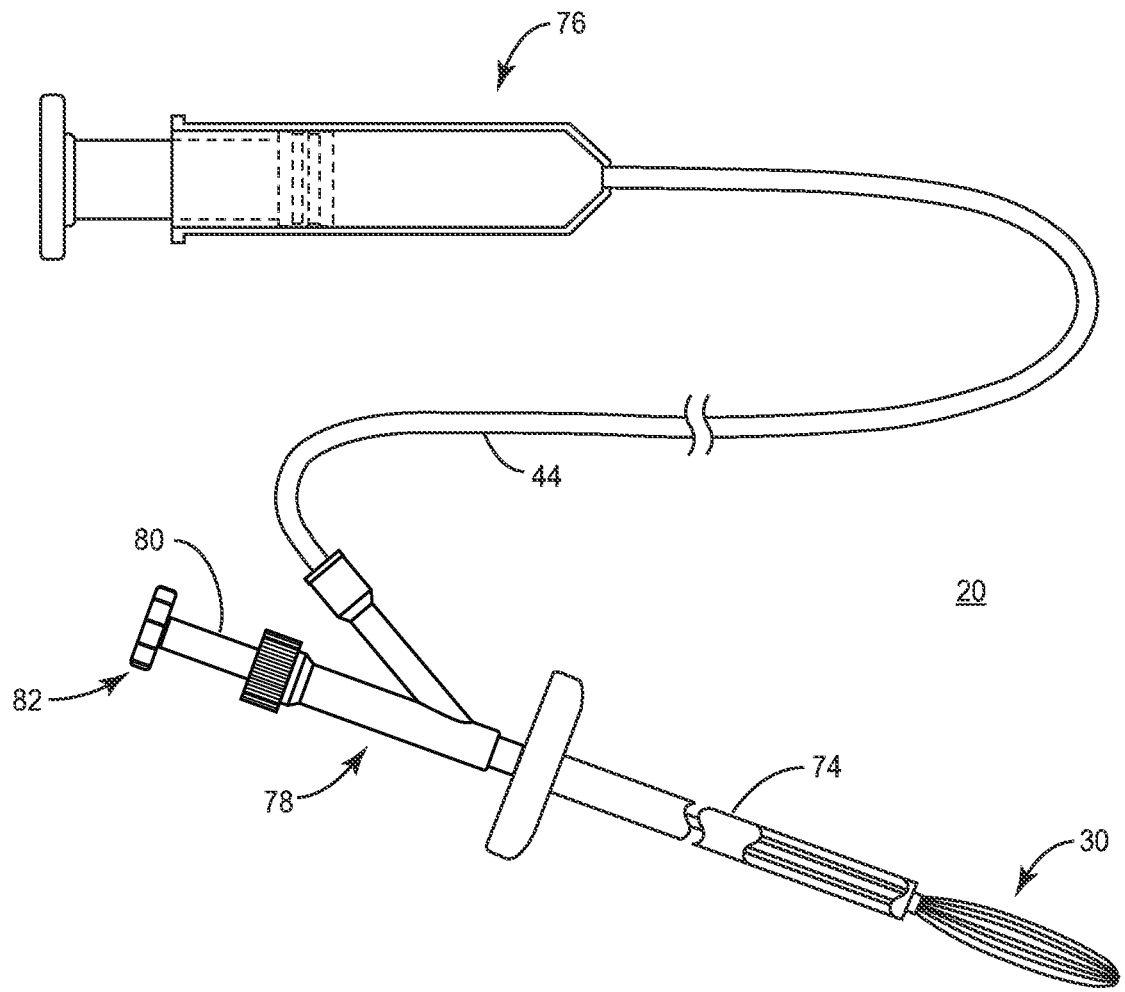
FIG. 1 is a perspective view of one embodiment of components of an inflatable balloon system in accordance with the principles of the present disclosure, in part cross section.

The exemplary embodiments of the surgical system and related methods of use disclosed are discussed in terms of medical devices for the treatment of musculoskeletal disorders and more particularly, in terms of a surgical system and method for bone repair. It is envisioned that the surgical system and method may be employed in applications such as for correction of fractures, depressions and breaks. For example, the surgical system and method can include inflatable bone tamps (IBTs) comprising an inflatable member having a reduced profile when in an unexpanded configuration to facilitate insertion of the inflatable member into a cannula and/or removal of the inflatable member from the cannula.

In one embodiment, the system and method include an inflatable bone tamp that includes a balloon made from polyurethane material. The balloon is configured to create a void or space in tissue, such as, for example, bone prior to delivering bone cement into the bone. In one embodiment, the bone is a vertebral body. The inflatable bone tamp includes a cannula configured to deliver the balloon to a surgical site, such as, for example the bone void. In one embodiment, the cannula has an inner diameter of approximately 4.0 mm. The balloon, when in an unexpanded configuration, has a profile which is greater than or equal to the diameter of the cannula. In order to reduce the profile of the balloon when the balloon is in the unexpanded configuration, while maximizing the size and wall thickness of the balloon, the IBT includes an inner support member, such as, for example, a stylet that extends through an inner cavity of the balloon. The stylet engages one end of the balloon such that translation of the stylet in a first direction causes the length of the balloon to increase. As the length of the balloon increases, the profile of the balloon decreases to facilitate disposal of the balloon in the cannula. That is, as the length of the balloon increases, an inner surface of the balloon moves toward an outer surface of the stylet such that the overall diameter of the balloon decreases.

In some embodiments, the stylet may be rotated about an axis defined by the stylet after increasing the length of the balloon. As the stylet rotates, the balloon twists about the outer surface of the stylet, thus further reducing the profile of the balloon. It is envisioned that reducing the profile of the balloon in the manner discussed herein will facilitate insertion of the balloon into the cannula and removal of the balloon from the cannula, when the balloon is in the unexpanded configuration. In some embodiments, the stylet may be rotated about an axis defined by the stylet without increasing the length of the balloon such that the balloon twists about the outer surface of the stylet to reduce the profile thereof.

In some embodiments, the IBT includes inner tubing extending into the balloon such that the balloon engages a distal end of the inner tubing. The inner tubing includes plastic tubing bonded into the distal end of the inner tubing. The stylet is movably disposed within the inner tubing and is configured to engage the plastic tubing. Translation of the stylet in a first direction causes the stylet to engage the plastic tubing while the stylet is translated in the first direction causing the length of the balloon to increase. As the length of the balloon increases, the profile of the balloon decreases to facilitate withdrawal of the balloon through the cannula. That is, as the length of the balloon increases, an inner surface of the balloon moves toward an outer surface of the inner tubing such that the overall diameter of the balloon decreases.

In some embodiments, a distal end of the stylet has a stepped configuration such that a first portion of the stylet has a first diameter and is configured for withdrawal in an opening defined by the plastic tubing and a second portion of the stylet adjacent the first portion has a second diameter that is greater than the first diameter, the second diameter being greater than the opening defined by the plastic tubing. This configuration allows the second portion of the stylet to engage the plastic tubing to prevent the first portion of the stylet from advancing through the opening defined by the plastic tubing. That is, force generated from translating the stylet through the inner tubing in the first direction causes the length of the balloon to increase and the profile of the balloon to decrease.

In some embodiments, the opening defined by the plastic tubing and the first portion of the stylet each have a configuration, such as, for example, a hexagonal configuration or a hexalobe configuration, configured to engage one another to prevent rotation of the stylet relative to the plastic tubing. This configuration allows the stylet to be rotated about an axis defined by the stylet such that the balloon twists about the outer surface of the inner tubing, thus reducing the profile of the balloon.

In some embodiments, the IBT includes one or a plurality of radiopaque marker bands positioned at a distal end of the inner tubing adjacent the plastic tubing to aid in measuring internal dimensions of the IBT and/or aid in positioning of the balloon relative to the surgical site. In some embodiments, the marker band(s) comprise a metallic material. In one embodiment, the marker band(s) comprise gold. In one embodiment, the marker band(s) comprise platinum. It is envisioned that the marker band(s) may be positioned at various locations of the IBT, such as, for example, the stylet and/or the balloon.

It is contemplated that one or all of the components of the surgical system may be disposable, peel-pack, pre-packed sterile devices. One or all of the components of the surgical system may be reusable. The surgical system may be configured as a kit with multiple sized and configured components, such as, for example, balloons that are preformed to have different sizes and shapes.

It is envisioned that the present disclosure may be employed to treat bones, and in particular spinal bones such as vertebrae. It should be understood that the present principles are applicable to any bone structures, including but not limited to bones of the spine, legs, feet, arms, etc. It is contemplated that the present disclosure may be employed with other osteal and bone related applications, including those associated with diagnostics and therapeutics. It is further contemplated that the disclosed surgical system and methods may alternatively be employed in a surgical treatment with a patient in a prone or supine position, and/or employ various surgical approaches, including anterior, posterior, posterior mid-line, direct lateral, postero-lateral, antero-lateral, etc. approaches in the calcaneus, spine or other body regions. The present disclosure may also be alternatively employed with procedures for treating the muscles, ligaments, tendons or any other body part. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following disclosure includes a description of a surgical system for treating fractures, including an inflation source, an inflatable bone tamp (IBT), employing drills and delivering bone void filler. In one embodiment, the bone void filler is bone cement, such as, for example, a material comprising polymethylmethacrylate (PMMA). The disclosure also includes a description of related methods of employing an expandable device. Alternate embodiments are also disclosed. Reference will now be made in detail to the exemplary embodiments of the present disclosure, which are illustrated in the accompanying figures. Turning now to FIGS. 1-5, there are illustrated components of a surgical system, such as, for example, an inflatable balloon system 20 and embodiments in accordance with the principles of the present disclosure.

The components of balloon system 20 can be fabricated from biologically acceptable materials suitable for medical applications, including metals, synthetic polymers, ceramics and bone material and/or their composites, depending on the particular application and/or preference of a medical practitioner. For example, the components of balloon system 20, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of balloon system 20 may have material composites, including the above materials, to achieve various desired characteristics such as strength, rigidity, elasticity, compliance, biomechanical performance, durability and radiolucency or imaging preference. The components of balloon system 20, individually or collectively, may also be fabricated from a heterogeneous material such as a combination of two or more of the above-described materials. The components of correction system 20 may be monolithically formed, integrally connected or include fastening elements and/or instruments, as described herein.

Balloon system 20 is employed, for example, with an open, mini-open or minimally invasive surgical technique to attach move or apply pressure to a bone fragment, fracture or surface, such as, in treating calcaneus fractures. Balloon system 20 includes an outer member 22 extending along an elongated axis A and comprising an inner surface 24 defining a first passageway 26. Passageway 26 extends the entire length of member 22 and has a cylindrical cross sectional configuration having a uniform diameter along the length of passageway 26. In some embodiments, passageway 26 may have alternate cross section configurations, such as, for example, oval, oblong, triangular, square, hexagonal, polygonal, irregular, uniform, non-uniform and/or tapered.

Member 22 comprises a compliant material, such as, for example, polyurethane, pellethane, polyethylene, silicone, cronoprene or non-compliant material such as Nylon. Member 22 has a first thickness defined by the distance between surface 24 an outer surface 28 of member 22. The first thickness is uniform along the length of member 22. In some embodiments, the thickness of member 22 is non-uniform. That is, the thickness of member 22 may vary along the length of member 22.

Figure 2:
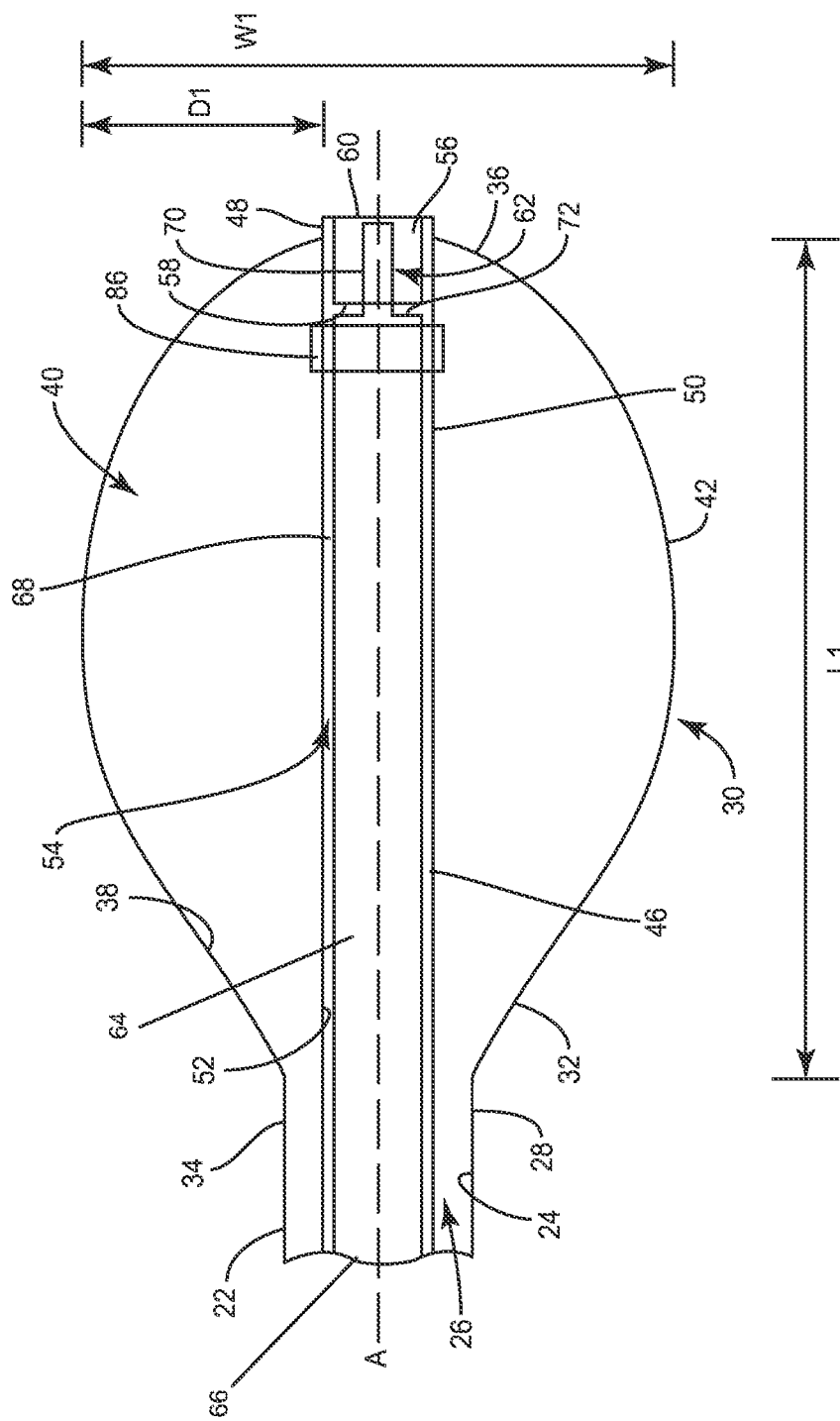
FIG. 2 is a side, cross sectional view of components of the system shown in FIG. 1 where an expandable member has a first profile and a first length.

An inflatable member, such as, for example, a balloon 30 has a proximal end 32 extending from a first end 34 of member 22 and a distal end 36. Balloon 30 has a length defined by the distance between end 34 and end 36. Balloon 30 has an inner surface 38 defining a chamber 40 extending the entire length of balloon 30. Surface 38 is continuous with surface 24 such that chamber 40 surrounds stylet 64. Member 22 may be attached to a fill tube 44 such that a material, such as, for example, saline, a contrast solution or compressed air may be delivered from tube 44, through the passageway 26 and into chamber 40. As the material fills chamber 40, balloon moves from an unexpanded configuration, shown in FIG. 3 to an expanded configuration, shown in FIG. 2. Removal of the material from chamber 40 thus causes balloon 30 to move from the expanded configuration shown in FIG. 2 to the unexpanded configuration shown in FIG. 3. As shown in FIG. 2, chamber 40 is configured to have a balloon shape when in the expanded configuration. It is envisioned that the shapes and sizes of balloon 30 when in the expanded configuration can be selected to provide a desired result during a procedure. For example, balloon 30 may include shapes such as spheres, cylinders, etc. and have different dimensions to make balloon 30 narrower or wider in a longitudinal direction, or extend further in a radial direction, etc.

Balloon 30 comprises a compliant material, such as, for example, polyurethane, pellethane, polyethylene, silicone, cronoprene or non-compliant material such as Nylon. Balloon 30 has a second thickness defined by the distance between surface 38 and outer surface 42 of balloon 30. In some embodiments, the second thickness is equal to or greater than the first thickness. In one embodiment, the second thickness is less than the first thickness.

It is envisioned that balloon 30 can be a single or multi-layered balloon where each balloon layer has the same diameter and/or wall thickness, is comprised of the same material or materials having substantially identical mechanical properties, and has the same degree of molecular orientation in the body portion of the balloon. It will be apparent that in some situations it will be desirable to have some balloon layers having different thicknesses, materials, and/or degree of molecular orientations upon deflation, while at the same time having equivalent size, mechanical properties, and/or orientation upon inflation or expansion. For other applications, it will be apparent that one can vary size, material, and/or orientation to at least some degree, depending upon the requirements of a particular application.

It is contemplated that balloon 30 may include an impenetrable structural layer having low friction surfaces so as to facilitate deployment through a delivery tube, such as, for example, through a lumen of a cannula 74 and prevent rupture of balloon 30 as it is inflated or expanded in situ. Further variations are contemplated involving different combinations of lubricating layers and structural layers. In some embodiments, structural layers of balloon 30 can contain polyamides, polyesters, polyethylenes, polyurethanes, their co-polymers and combinations thereof.

It is envisioned that balloon 30 can be adapted to withstand the particular stresses, pressures, and deformities to which they might be placed under when inflated or expanded within a surgical site, such as, for example, a bone void in one or more vertebrae. For example, because a top (outer) layer of balloon 30 may be exposed to sharp objects (such as calcified plaque, bone, bone spurs, or other natural protrusions within a patient's body), the top layer could be made from a more compliant material that is scratch and puncture resistant, than the layer or layers below the top layer (inner layer(s)). That is, the top or outer layer is made from a more compliant material that is scratch and puncture resistant and the inner layers of the multi-layer balloon, which are generally not exposed to sharp objects, made from a less compliant material with a higher burst strength. It is contemplated that further variations are possible, depending on which stresses, pressures, and deformities the layers must withstand in a particular medical application.

Inner tubing, such as, for example, an inner member 46 is positioned within passageway 26 and chamber 40 such that a first end 48 of member 46 is coupled to end 36 of balloon 30. In some embodiments, end 36 of balloon 30 is tethered to an outer surface 50 of member 46. End 36 can be tethered to the surface 50 by any method of bonding or attachment, such as, for example, adhesive bonding or thermal bonding. In some embodiments, member 22, balloon 30 and member 46 are integrally formed. Laser bonding, RF bonding are some other bonding methods.

In some embodiments, member 46 includes one or a plurality of marker bands 86 comprising a radiopaque material. Bands 86 each include an inner surface configured to engage surface 50 to identify the position of balloon 30 relative to a distal end of cannula 74. It is envisioned that bands 86 can be located at regular intervals along the length of member 46 to aid in measuring internal dimensions or at selected structural locations to aid in positioning of balloon 30. In some embodiments, bands 86 are formed of polymeric material having highly radiopaque material incorporated therein. In one embodiment, the polymeric material is polyether block amide. In some embodiments, the highly radiopaque material incorporated into the polymeric material is barium sulfate, bismuth subcarbonate, tungsten, or a combination thereof.

Member 46 has an inner surface 52 defining a second passageway 54. Passageway 54 extends the entire length of member 46 and has a cylindrical cross sectional configuration having a uniform diameter along the length of passageway 54. In some embodiments, passageway 54 may have alternate cross section configurations, such as, for example, oval, oblong, triangular, square, hexagonal, polygonal, irregular, uniform, non-uniform and/or tapered.

Passageway 54 includes a stop member 56 disposed in end 48. In some embodiments, member 56 comprises plastic tubing or cured adhesive. Member 56 has an outer surface configured to engage surface 52 and a diameter that is substantially equivalent to a diameter of passageway 54 such that member 56 forms a plug that completely fills a portion of passageway 54 adjacent end 48. In some embodiments, member 56 is bonded to surface 52. Member 56 can be bonded to the surface 52 by any method of bonding or attachment, such as, for example, adhesive bonding or thermal bonding. In some embodiments, member 56 and member 46 are integrally formed, swagging or capped with adhesive.

Member 56 extends along axis A between a first end surface 58 and a second end surface 60. An inner surface of member 56 defines a blind hole, such as, for example, an opening 62 extending parallel to axis A through surface 58 without extending through surface 60. In some embodiments, opening 62 may be variously configured and dimensioned, such as, for example, square, hexagonal, polygonal, star or hexalobe, irregular, uniform, non-uniform, staggered, tapered, consistent or variable, depending on the requirements of a particular application. In some embodiments, opening 62 may be disposed at alternate orientations relative to axis A, such as, for example, transverse, perpendicular and/or other angular orientations such as acute or obtuse, according to the requirements of a particular application.

A support member, such as, for example, a stylet 64 is movably disposed within passageway 54. In one embodiment, stylet is made from a molded plastic or a stainless steel material or Nitinol. In one embodiment, member 22, member 46 and balloon 30 are made from a material or materials having a lower modulus of elasticity (that is/are less stiff) than a material or materials from which stylet 64 and cannula 74 are made. In one embodiment, at least one of member 22, member 46 and balloon 30 are made entirely of a single material having a modulus of elasticity (Young's modulus) in the range of about $1.0\times10^2$ to about $6.0\times10^5$ dynes/cm$^2$, or about $2.0\times10^4$ to about $5.0\times10^5$ dynes/cm$^2$, or about $5.0\times10^4$ to about $5.0\times10^5$ dynes/cm$^2$. In one embodiment, the material or materials that forms/form member 22, member 46, balloon 30 is/are treated to impart a desired modulus of elasticity within the ranges discussed above.

Stylet 64 includes a first end 66 configured for disposal in opening 62. End 66 includes a first portion 68 having a first diameter and a second portion 70 extending from portion 68 having a second diameter that is less than the first diameter. Portions 68, 70 defined a stepped portion of stylet 64. An interface between portions 68, 70 defines an engaging surface 72 extending transverse to axis A. The first diameter is greater than a diameter of opening 62 and the second diameter is less than the diameter of opening 62 such that surface 72 engages surface 58 when portion 70 is fully inserted into opening 62. Portion 70 has a configuration adapted to closely engage opening 62. In some embodiments, portion 70 may be variously configured and dimensioned, such as, for example, square, hexagonal, polygonal, star or hexalobe, irregular, uniform, non-uniform, staggered, tapered, consistent or variable, depending on the requirements of a particular application. In some embodiments, surface 72 may be disposed at alternate orientations relative to axis A, such as, for example, transverse, perpendicular and/or other angular orientations such as acute or obtuse, according to the requirements of a particular application.

In some embodiments, portion 70 has a configuration that mates with the configuration of opening 62 to prevent rotation of portion 70 within opening 62. The mating configurations prevent rotation of stylet 64 relative to member 46 such that rotation of stylet 64 about axis in the direction shown by arrow B or the direction shown by arrow BB causes member 46 to rotate in the direction shown by arrow B or the direction shown by arrow BB, respectively. Because balloon 30 is bonded to surface 50, rotation of member 46 about axis A in the direction shown by arrow B or the direction shown by arrow BB causes balloon 30 to rotate in the direction shown by arrow B or the direction shown by arrow BB, respectively. Rotation of balloon 30 causes balloon 30 to twist about surface 50. In some embodiments, balloon 30 includes at least one fold, such as, for example, crinkles, creases, ruffles, pleats, tucks or other such gathered segments so as to facilitate twisting of balloon 30 about surface 50 and provide for a profile that is less than a profile of a twisted balloon that does not include the at least one fold.

A material, such as, for example, saline, a contrast solution or compressed air is delivered through tube 44 and passageway 26 and into chamber 40. As the material fills chamber 40, balloon 30 moves from an unexpanded configuration, shown in FIG. 3 to an expanded configuration, shown in FIG. 2. Balloon 30 has a length L1 and a maximum width W1 when in the expanded configuration such that surface 42 is spaced apart from surface 50 a distance D1, as shown in FIG. 2. Width W1 and distance D1 define a first profile of balloon 30.

Figure 3:
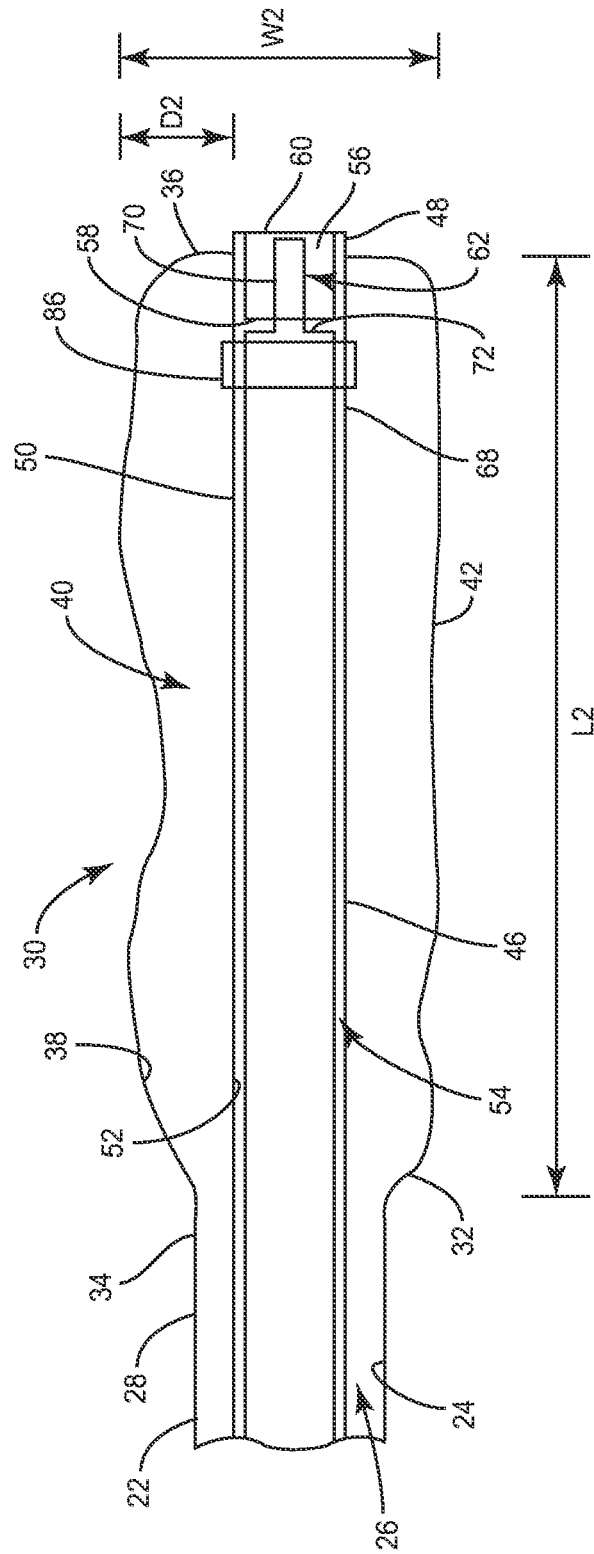
FIG. 3 is a side, cross sectional view of components of the system shown in FIG. 1 where the expandable member has a second profile that is less than the first profile and a second length that is equal to the first length.

Removal of the material from chamber 40 causes balloon 30 to move from the expanded configuration shown in FIG. 2 to the unexpanded configuration shown in FIG. 3. Balloon 30 has a length L2 and a maximum width W2 when in the unexpanded configuration such that surface 42 is spaced apart from surface 50 a distance D2, as shown in FIG. 3. Length L2 is equal to length L1, width W2 is less than width W1 and distance D2 is less than distance D1. Width W2 and distance D2 define a second profile of balloon 30.

Figure 4:
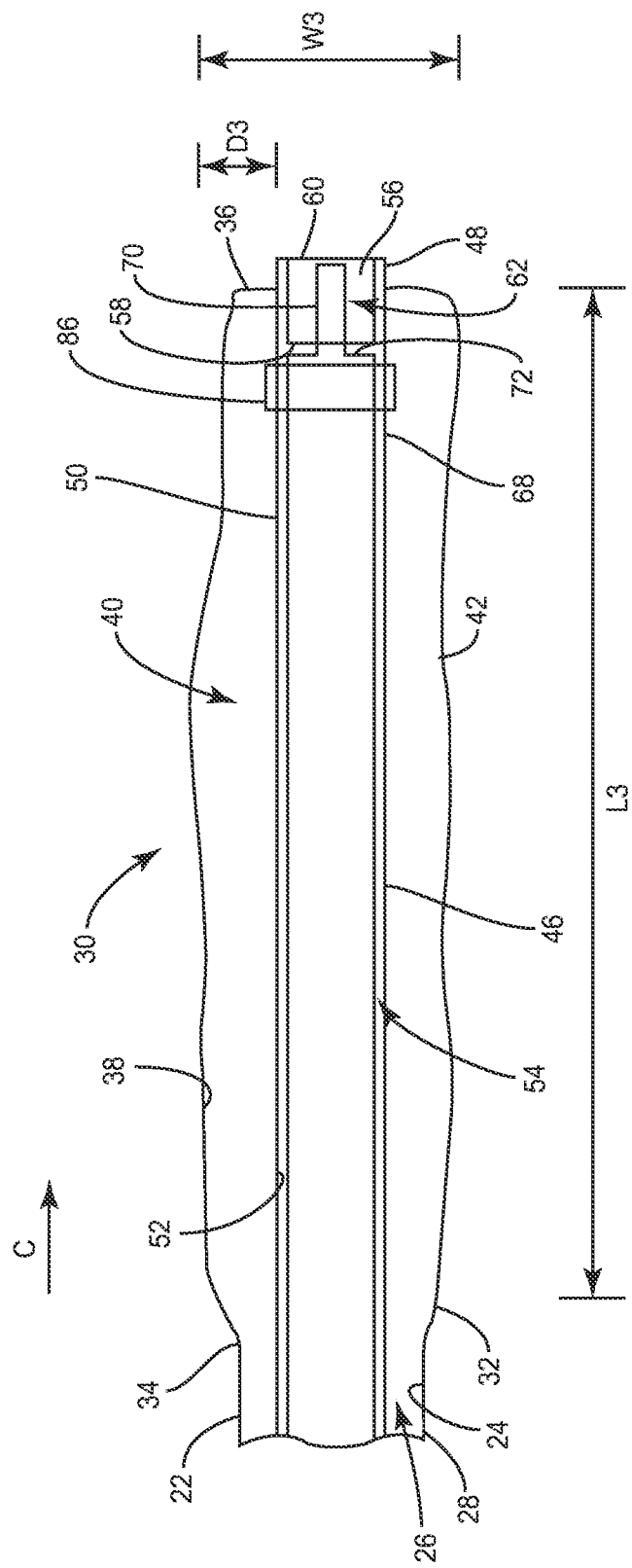
FIG. 4 is a side, cross sectional view of components of the system shown in FIG. 1 where the expandable member has a third profile that is less than the second profile and a third length that is greater than the first length and the second length.

Stylet 64 may be translated along axis A in a first direction, such as, for example, the direction shown by arrow C until portion 70 is disposed within opening 62 and surface 72 engages surface 58. Stylet 64 is further translated along axis A in the direction shown by arrow C such that the length of balloon 30 increases from length L2 to length L3, as shown in FIG. 4. As the length of balloon 30 increases from length L2 to length L3, the maximum width of balloon 30 decreases from width W2 to width W3 such that surface 42 is spaced apart from surface 50 a distance D3, that is less than distance D2. Width W3 and distance D3 define a third profile of balloon 30. The third profile of balloon 30 is less than the second profile of balloon 30 to facilitate insertion/withdrawal of balloon 30 into cannula 74. In some embodiments, cannula 74 has an inner diameter that is greater than width W2, but less than width W3, such that balloon 30 must be moved from the second profile shown in FIG. 3 to the third profile shown in FIG. 4 in order to insert/withdrawal balloon 30 into cannula 74.

Figure 5:
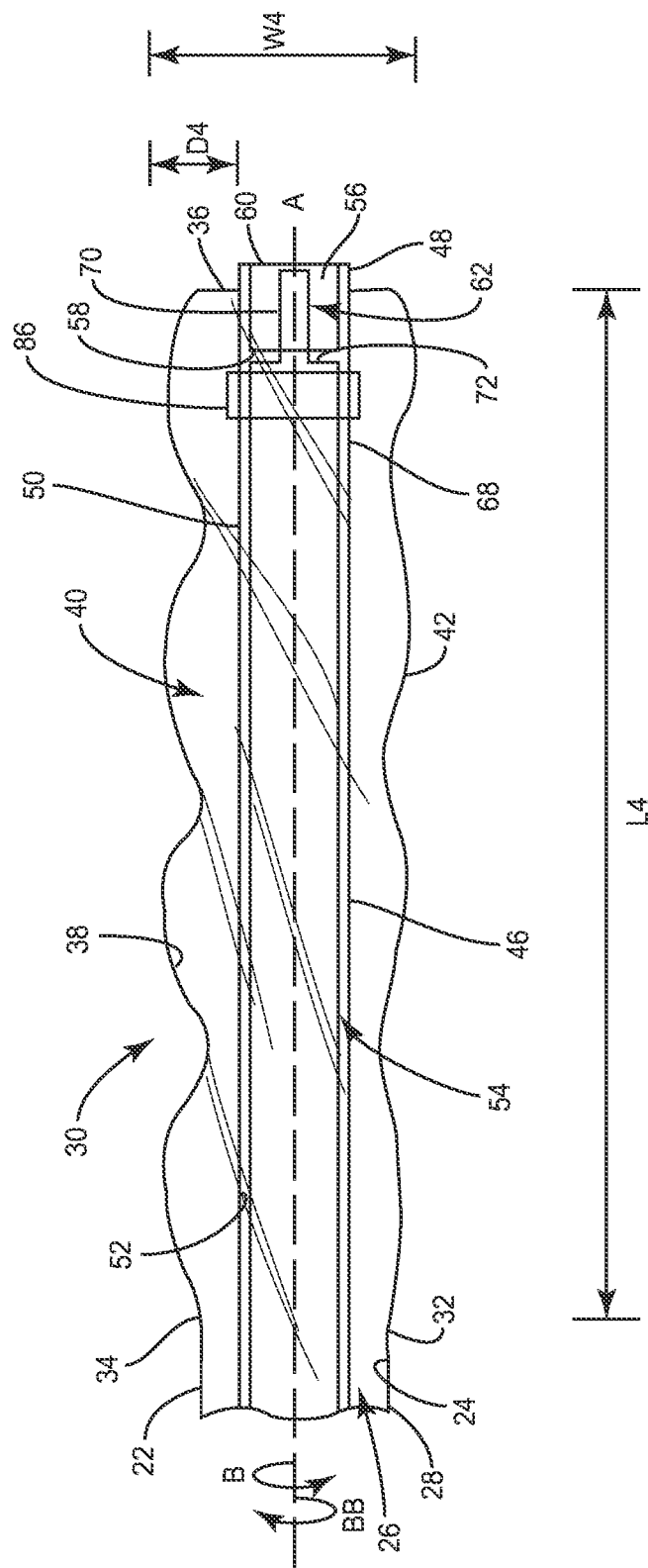
FIG. 5 is a side, cross sectional view of components of the system shown in FIG. 1 where the expandable member has a fourth profile that is less than the third profile and a fourth length that is equal to the third length.

In embodiments in which portion 70 has a configuration that mates with the configuration of opening 62 to prevent rotation of portion 70 within opening 62, member 46 may be rotated about axis A in the direction shown by arrow B or the direction shown by arrow BB such that balloon 30 rotates in the direction shown by arrow B or the direction shown by arrow BB, respectively. Rotation of balloon 30 causes balloon 30 to twist about surface 50 such that balloon 30 has a maximum width W4 and surface 42 is spaced apart from surface 50 a distance D4, as shown in FIG. 5. Width W4 is less than width W3 and distance D4 is less than distance D3. Width W4 and distance D4 define a fourth profile of balloon 30. The fourth profile of balloon 30 is less than the third profile of balloon 30 to facilitate insertion of balloon 30 into cannula 74. In some embodiments, cannula 74 has an inner diameter that is greater than width W3, but less than width W4, such that balloon 30 must be moved from the third profile shown in FIG. 4 to the fourth profile shown in FIG. 5 in order to insert balloon 30 into cannula 74. Balloon 30 has a length L4 when in the fourth profile, length L4 being equal to length L3.

In some embodiments, a portion of stylet 64 is disposed in a third passageway defined by an inner surface of an inflation member, such as, for example, a Y-shaped connector tube 78. A second end 80 of stylet 64 opposite end 66 includes a cap 82 having an outer surface including a first locking surface, such as, for example a first thread form. Tube 78 has an inner surface defining a second locking surface, such as, for example, a second thread form configured to engage the first locking surface to prevent axial translation of stylet 64 relative to tube 78. This configuration allows the first and second locking surfaces to engage one another to maintain balloon 30 in the third profile shown in FIG. 4. In some embodiments cap 82 may be retained with tube 78 in alternate fixation configurations, such as, for example, friction fit, pressure fit, locking protrusion/recess, locking keyway and/or adhesive.

Figure 6:
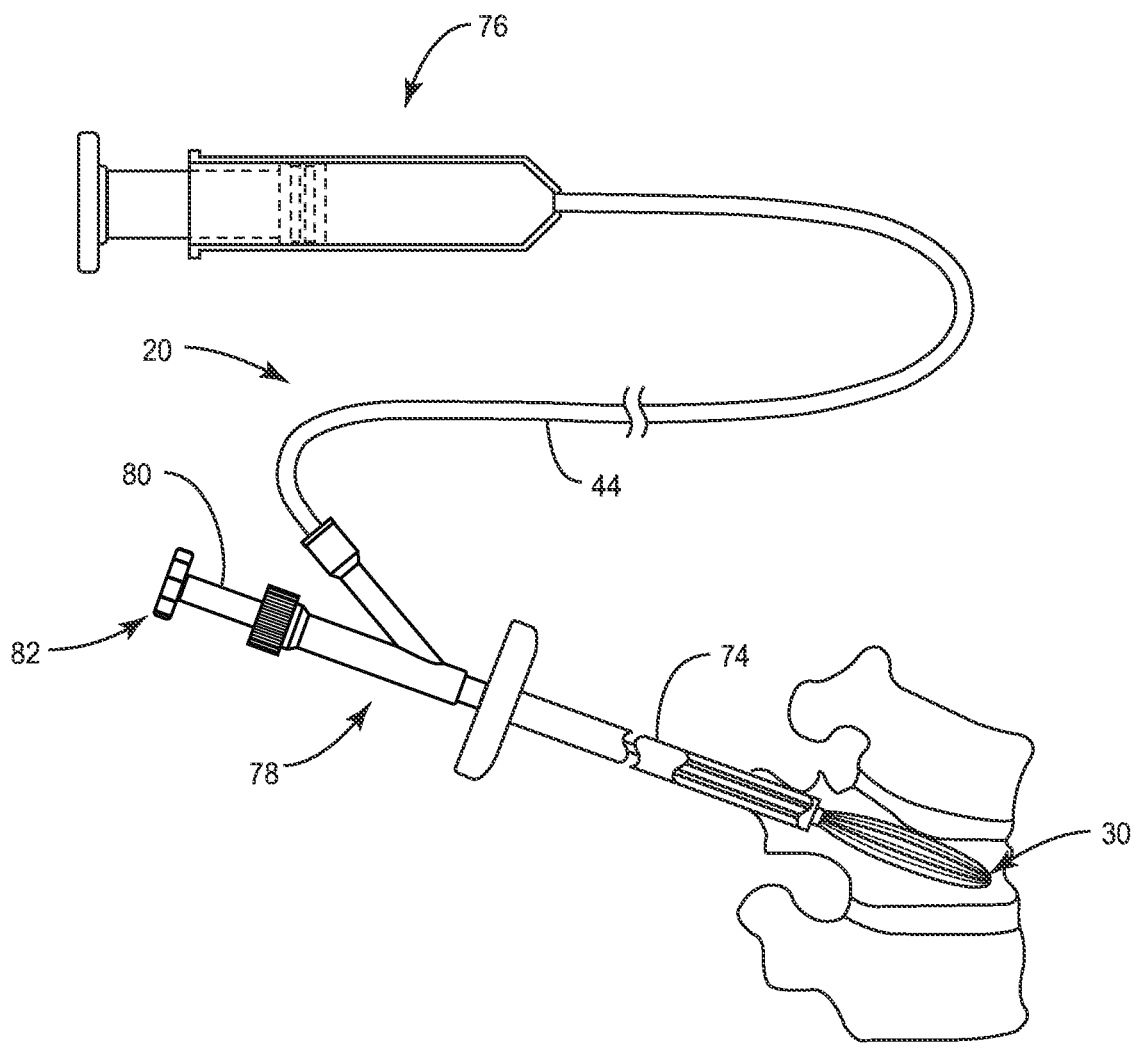
FIG. 6 is a plan view of the system shown in FIG. 1, with the expandable member disposed between adjacent vertebrae.

In assembly, operation and use, system 20 is employed with a surgical procedure, such as, for a correction or treatment of bone fractures. It is contemplated that one or all of the components of system 20 can be delivered or implanted as a pre-assembled device or can be assembled in situ. System 20 may be completely or partially revised, removed or replaced. For example, as shown in FIG. 6, system 20 can be employed with a surgical correction treatment of an applicable condition or injury of an affected portion of a patient, such as, for example, an intervertebral space. It is envisioned that system 30 may also be used to treat other affected portions of the patient, such as, for example, a calcaneus bone, bones of the feet or hands, bones of the spine, bones of the arms and legs, etc.

In use, to treat a fracture, a medical practitioner obtains access to a surgical site including the fractured bone in any appropriate manner, such as through incision and retraction of tissues. In one embodiment, a drill is employed to remove bone tissue to provide access to a repair site. It is envisioned that system 20 can be used in any existing surgical method or technique including open surgery, mini-open surgery, minimally invasive surgery and percutaneous surgical implantation, whereby the fractured or injured bone is accessed through a mini-incision or sleeve that provides a protected passageway to the area. Once access to the surgical site is obtained, the particular surgical procedure can be performed for treating the injury or disorder. The configuration and dimension of system 20 is determined according to the configuration, dimension and location of a selected section of the bone fracture and the requirements of a particular application.

An incision is made in the body of a patient and a cutting instrument (not shown) creates a surgical pathway for implantation of components of system 20. This may include the use of a cannula or other device. A preparation instrument (not shown) can be employed to prepare tissue surfaces, as well as for aspiration and irrigation of a surgical region according to the requirements of a particular surgical application.

Balloon 30 may be inserted into cannula 74 when balloon 30 has the second profile shown in FIG. 3, the third profile shown in FIG. 4 or the fourth profile shown in FIG. 5. Tube 44 may then be coupled to an inflation device 76. In some embodiments, inflation device 76 may include one or a plurality of syringes, gas pumps, compressed gas cartridges, etc. In one embodiment, inflation device 76 includes a single gas source with a manifold and independently controlled valves such that the valves may be employed in controlled pressurized fluid flow to balloon Other inflation methods are also contemplated. Inflation device 76 is configured to provide a particular pressure, volume and/or fill rate to balloon 30. The control of the pressurized fluid may be performed manually or automatically.

Automatic control may include the use of a computer interface or controller device (not shown) to set the pressure, volume and/or fill rate automatically based upon a geometric profile desired. For example, one or more of these parameters for balloon 30 in the desired composite profile, including relative sizes, pressure/volume and fill speeds, may be controlled and adjusted. The individually controlled inflation volumes are controlled, e.g., using a syringe(s) or pump(s).

A material, such as, for example, saline, a contrast solution or compressed air may be delivered from device 76, through tube 44 and passageway 26 and into chamber 40. The material may be delivered into chamber 40 until balloon assumes the first profile shown in FIG. 2 (until balloon 30 is in the expanded configuration). Moving balloon 30 to the first profile causes surface 42 to push against bone that defines the surgical site, such as, for example, cancellous bone such that balloon 30 creates a void in the bone.

Removal of the material from chamber 40 causes balloon 30 to move from the expanded configuration shown in FIG. 2 to the unexpanded configuration shown in FIG. 3. In addition, a negative pressure can be applied to balloon 30 once in the unexpanded configuration so as to reduce the profile of balloon and/or aid in the withdrawal of balloon 30 from the surgical site. In order to insert balloon 30 in cannula 74 to remove system 20 from the patient, stylet 64 may be translated along axis A in the direction shown by arrow C until portion 70 is disposed within opening 62 and surface 72 engages surface 58. Stylet 64 is further translated along axis A in the direction shown by arrow C such that the length of balloon 30 increases from length L2 to length L3, as shown in FIG. 4. As the length of balloon 30 increases from length L2 to length L3, the maximum width of balloon 30 decreases from width W2 to width W3 such that surface 42 is spaced apart from surface 50 a distance D3, that is less than distance D2. The first and second locking surfaces of cap 82 and tube 78 may be moved to engage one another to maintain balloon 30 in the third profile shown in FIG. 4.

In some embodiments, in which portion 70 has a configuration that mates with the configuration of opening 62 to prevent rotation of portion 70 within opening 62, member 46 may be rotated about axis A in the direction shown by arrow B or the direction shown by arrow BB such that balloon 30 rotates in the direction shown by arrow B or the direction shown by arrow BB, respectively. Rotation of balloon 30 causes balloon 30 to twist about surface 50 such that balloon 30 has a maximum width W4 and surface 42 is spaced apart from surface 50 a distance D4, as shown in FIG. 5. In some embodiments, cannula 74 has an inner diameter that is greater than width W3, but less than width W4, such that balloon 30 must be moved from the third profile shown in FIG. 4 to the fourth profile shown in FIG. 5 in order to insert balloon 30 into cannula 74. Accordingly, once balloon 30 has the fourth profile, balloon 30 may be inserted into cannula 74 and balloon 30 removed from cannula 74.

Following removal of balloon 30 from cannula 74, the bone void created by expansion of balloon 30 in the surgical site is filled with a bone void filler, such as, for example, autograft, allograft, demineralized bone matrix, mineral composites, blocks, granules and pellets and bone cement, such as, for example, polymethylmethacrylate (PMMA)-based material (Kyphon HV-R, ActivOs, ActivOs 10, Xpede), calcium phosphate (Skaffold, Norian, Hydroset, KyphOs FS) and calcium sulfate (OsteoSet), as well as other injectables. Shortly after filling the bone void with the bone void filler, the bone void filler hardens or polymerizes, desirably supporting the vertebral bodies defining the intervertebral space internally, alleviating pain and preventing further collapse.

In one embodiment, shown in FIGS. 7-10, system 20 includes an outer member 122 similar to member 22 extending along an elongated axis A1 and comprising an inner surface 124 defining a first passageway 126. Member 122 comprises a compliant material, such as, for example, polyurethane.

An inflatable member, such as, for example, a balloon 130 similar to balloon 30 has a proximal end 132 extending from a first end 134 of member 122 and a distal end 136. Balloon 130 has a length defined by the distance between end 134 and end 136. Balloon 130 has an inner surface 138 defining a chamber 140. Member 122 may be attached to a tube, such as, for example, fill tube 44 such that a material, such as, for example, saline, a contrast solution or compressed air may be delivered from tube 44, through the passageway 126 and into chamber 140. As the material fills chamber 140, balloon 130 moves from an unexpanded configuration, shown in FIG. 8 to an expanded configuration, shown in FIG. 7. Removal of the material from chamber 140 thus causes balloon 130 to move from the expanded configuration shown in FIG. 7 to the unexpanded configuration shown in FIG. 8.

A support member, such as, for example, a stylet 164 similar to stylet 64 is movably disposed within passageway 126 and chamber 140. Stylet 164 includes a first end 166 coupled to end 136 of balloon 130. In some embodiments, end 136 of balloon 130 is tethered to an outer surface 184 of stylet 164. End 136 can be tethered to the surface 184 by any method of bonding or attachment, such as, for example, adhesive bonding or thermal bonding. In some embodiments, member 122, balloon 130 and stylet 164 are integrally formed.

Because balloon 130 is bonded to surface 184, rotation of stylet 164 about axis A1 in the direction shown by arrow D or the direction shown by arrow DD causes balloon 130 to rotate in the direction shown by arrow D or the direction shown by arrow DD, respectively. Rotation of balloon 130 causes balloon 130 to twist about surface 184. In some embodiments, balloon 130 includes at least one fold, such as, for example, crinkles, creases, ruffles, pleats, tucks or other such gathered segments so as to facilitate twisting of balloon 130 about surface 184 and provide for a profile that is less than a profile of a twisted balloon that does not include the at least one fold.

Figure 7:
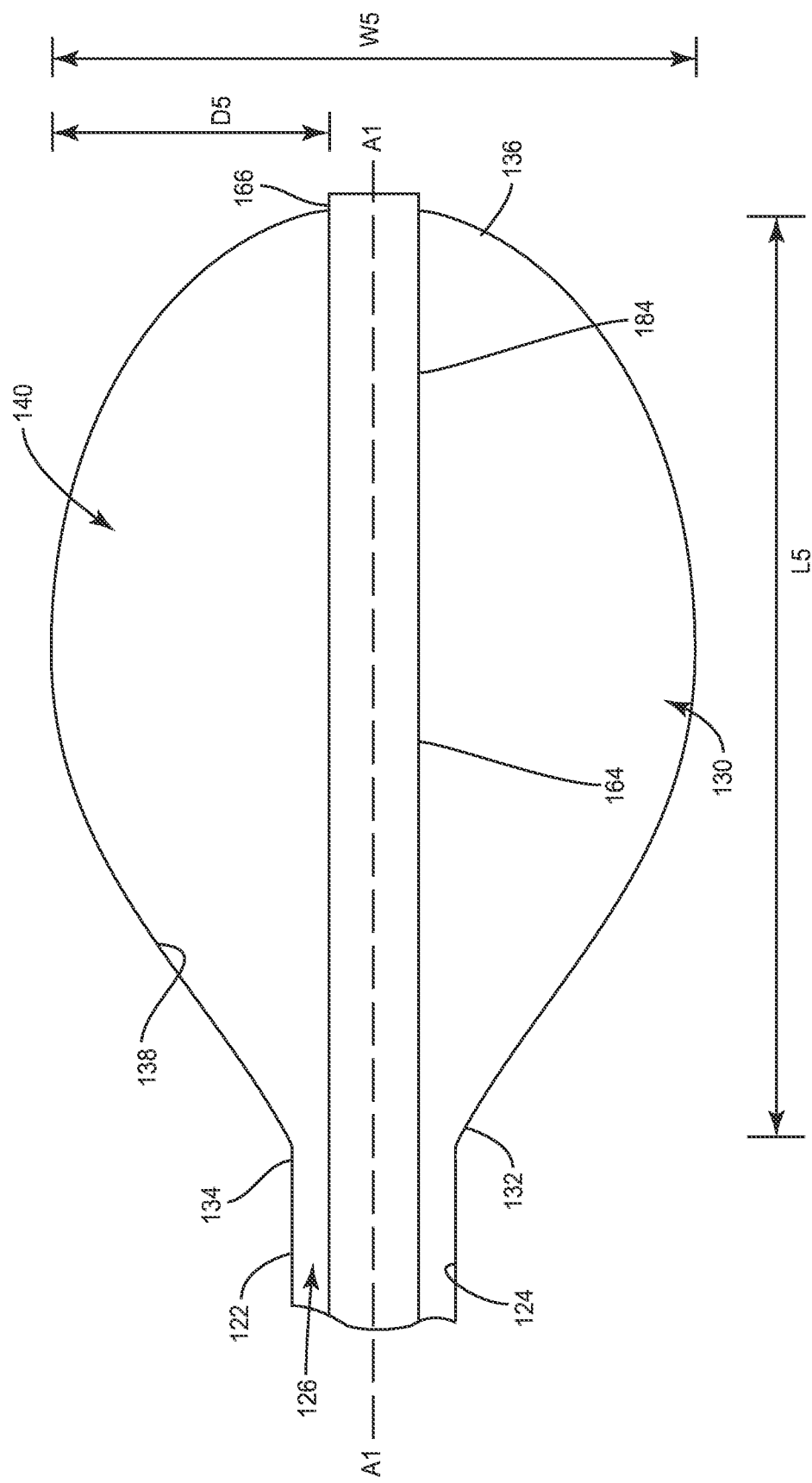
FIG. 7 is a side, cross sectional view of components of an inflatable balloon system in accordance with the principles of the present disclosure where an expandable member has a first profile and a first length.

A material, such as, for example, saline, a contrast solution or compressed air is delivered through tube 44 and passageway 126 and into chamber 140. As the material fills chamber 140, balloon 130 moves from an unexpanded configuration, shown in FIG. 8 to an expanded configuration, shown in FIG. 7. Balloon 130 has a length L5 and a maximum width W5 when in the expanded configuration such that surface 138 is spaced apart from surface 184 a distance D5, as shown in FIG. 7. Width W5 and distance D5 define a first profile of balloon 130.

Figure 8:
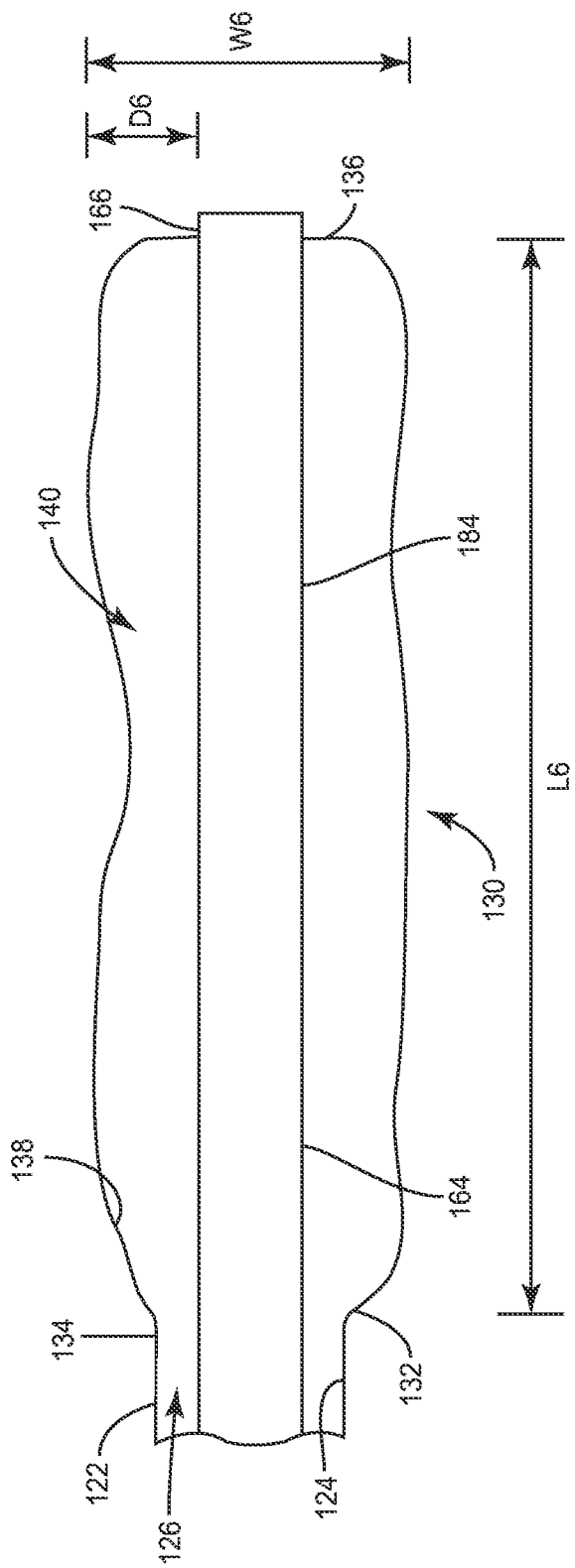
FIG. 8 a side, cross sectional view of components of the system shown in FIG. 7 where the expandable member has a second profile that is less than the first profile and a second length that is equal to the first length.

Removal of the material from chamber 140 causes balloon 130 to move from the expanded configuration shown in FIG. 7 to the unexpanded configuration shown in FIG. 8. Balloon 130 has a length L6 and a maximum width W6 when in the unexpanded configuration such that surface 138 is spaced apart from surface 184 a distance D6, as shown in FIG. 8. Length L6 is equal to length L5, width W6 is less than width W5 and distance D6 is less than distance D5. Width W6 and distance D6 define a second profile of balloon 130.

Figure 9:
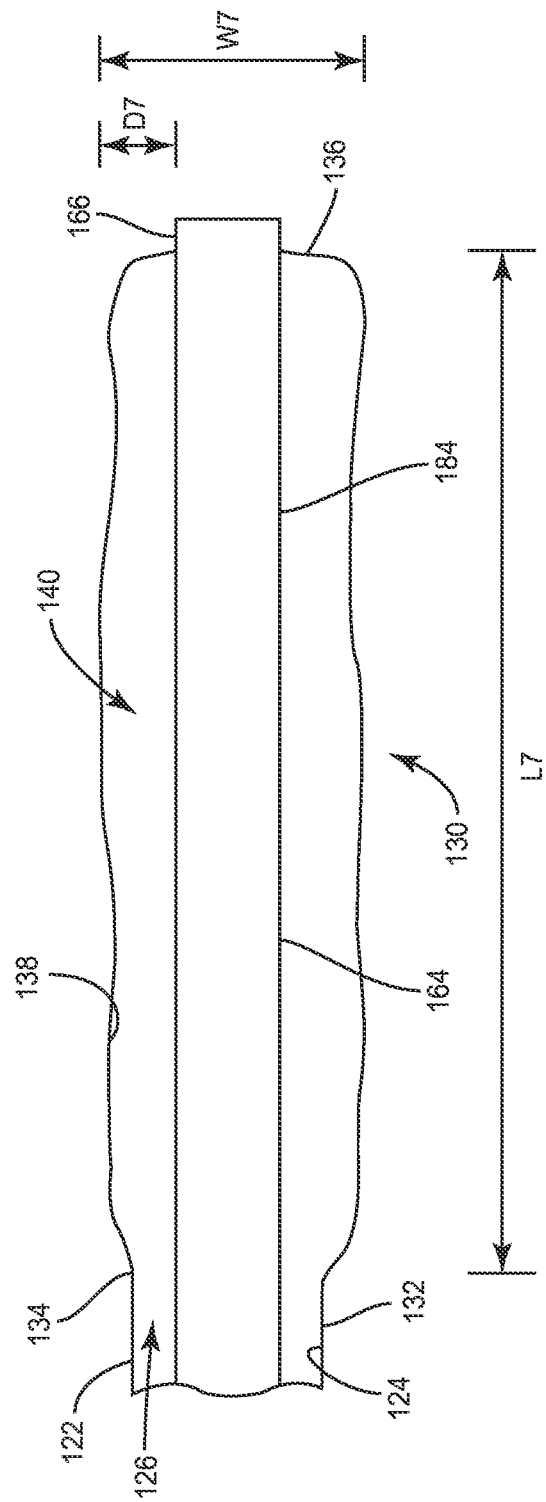
FIG. 9 is a side, cross sectional view of components of the system shown in FIG. 7 where the expandable member has a third profile that is less than the second profile and a third length that is greater than the first length and the second length.

Stylet 164 may be translated along axis A1 in a first direction, such as, for example, the direction shown by arrow E such that the length of balloon 130 increases from length L6 to length L7, as shown in FIG. 9. As the length of balloon 130 increases from length L6 to length L7, the maximum width of balloon 130 decreases from width W6 to width W7 such that surface 138 is spaced apart from surface 184 a distance D7, that is less than distance D6. Width W7 and distance D7 define a third profile of balloon 130. The third profile of balloon 130 is less than the second profile of balloon 130 to facilitate insertion of balloon 130 into cannula 74. In some embodiments, cannula 74 has an inner diameter that is greater than width W6, but less than width W7, such that balloon 130 must be moved from the second profile shown in FIG. 8 to the third profile shown in FIG. 9 in order to insert balloon 130 into cannula 74.

Figure 10:
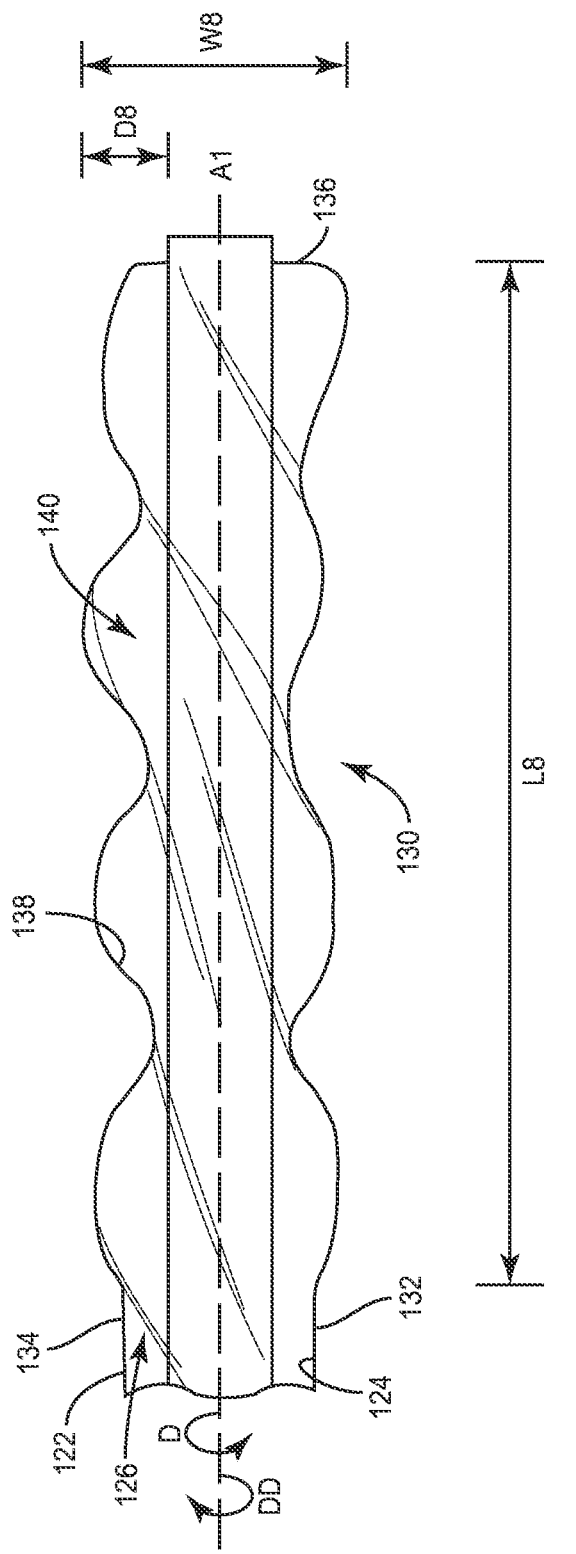
FIG. 10 is a side, cross sectional view of components of the system shown in FIG. 1 where the expandable member has a fourth profile that is less than the third profile and a fourth length that is equal to the third length.

Stylet 164 may be rotated about axis A1 in the direction shown by arrow D or the direction shown by arrow DD such that balloon 130 rotates in the direction shown by arrow D or the direction shown by arrow DD, respectively. Rotation of balloon 130 causes balloon 130 to twist about surface 184 such that balloon 130 has a maximum width W8 and surface 138 is spaced apart from surface 184 a distance D8, as shown in FIG. 10. Width W8 is less than width W7 and distance D8 is less than distance D7. Width W8 and distance D8 define a fourth profile of balloon 130. When balloon 130 has the fourth profile, balloon 130 has a length L8 that is equal to length L7. The fourth profile of balloon 130 is less than the third profile of balloon 130 to facilitate insertion of balloon 130 into cannula 74. In some embodiments, cannula 74 has an inner diameter that is greater than width W7, but less than width W8, such that balloon 130 must be moved from the third profile shown in FIG. 9 to the fourth profile shown in FIG. 10 in order to insert balloon 130 into cannula 74.

In one embodiment, system 20 includes an agent, which may be disposed, packed or layered within, on or about the components and/or surfaces of the components of system 20. It is envisioned that the agent may include bone growth promoting material, such as, for example, bone graft to enhance fixation of the fixation elements with the bone in need of repair. It is further contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of system 20 can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. The balloon can be modified or extended to accommodate particular formulations of balloon construction materials or fabrication techniques. Different balloon materials and surface coatings, or outer layers of different materials or surface coatings may also be applied to the balloon to facilitate a smaller balloon profile, biocompatibility, lubrication as well as other properties. The embodiments above can also be modified so that some features of one embodiment are used with the features of another embodiment. One skilled in the art may find variations of these preferred embodiments, which, nevertheless, fall within the spirit of the present invention, whose scope is defined by the claims set forth below.

What is claimed is:

1. A surgical device comprising:
   a sleeve;
   a shaft disposed in the sleeve, the shaft defining a passageway;
   a stopper disposed in the passageway;
   a balloon having a first end coupled to the sleeve and a second end coupled to the shaft, the balloon defining a chamber; and
   a support member disposed within the passageway and moveable relative to the shaft between a first position in which an end of the support member is spaced apart from the stopper and a second position in which the end of the support member is positioned within the stopper.

2. The surgical device recited in claim 1, wherein the support member is prevented from rotating relative to the shaft when the support member is in the second position.

3. The surgical device recited in claim 1, wherein the end of the support member engages a surface of the stopper when the support member is in the second position to prevent the support member from rotating relative to the shaft.

4. The surgical device recited in claim 1, wherein the support member is configured to translate relative to the sleeve when the support member is in the second position to increase a length of the balloon.

5. The surgical device recited in claim 1, wherein rotation of the shaft relative to the sleeve when the support member is in the second position causes the balloon to twist about the shaft.

6. The surgical device recited in claim 1, wherein the stopper has an opening, the end of the support member including a stepped portion configured for disposal in the opening of the stopper when the support member is in the second position.

7. The surgical device recited in claim 6, wherein the opening and the stepped portion each have a configuration configured to engage one another to prevent rotation of the support member within the stopper when the support member is in the second position.

8. The surgical device recited in claim 6, wherein the opening and the stepped portion each have a polygonal configuration configured to engage one another to prevent rotation of the support member within the stopper when the support member is in the second position.

9. The surgical device recited in claim 6, wherein the opening and the stepped portion each have a configuration configured to engage one another to prevent rotation of the support member within the stopper when the support member is in the second position such that rotation of the shaft relative to the sleeve when the support member is in the second position causes the balloon to twist about the shaft.

10. The surgical device recited in claim 1, further comprising a marker band coupled to an outer surface of the shaft such that the marker band is spaced apart from the sleeve.

11. The surgical device recited in claim 1, wherein the sleeve is made from a material having a lower modulus of elasticity than a material from which the support member is made.

12. The surgical device recited in claim 1, wherein the shaft is made from a material having a lower modulus of elasticity than a material from which the support member is made.

13. The surgical device recited in claim 1, wherein the balloon is made from a material having a lower modulus of elasticity than a material from which the support member is made.

14. The surgical device recited in claim 1, wherein the passageway is coaxial with the channel.

15. The surgical device recited in claim 1, wherein the shaft comprises an inner surface defining the passageway, the stopper having an outer surface that directly engages the inner surface.

16. The surgical device recited in claim 1, wherein the stopper forms a plug that completely fills a portion of the passageway.

17. A surgical device comprising:
    a sleeve;
    a shaft disposed in the sleeve, the shaft defining a passageway;
    a stopper disposed in the passageway;
    a balloon having a first end coupled to the sleeve and a second end coupled to the shaft, the balloon defining a chamber; and
    a support member disposed within the passageway and moveable relative to the shaft between a first position in which an end of the support member is spaced apart from the stopper and a second position in which the end of the support member is positioned within the stopper,
    wherein the support member is prevented from rotating relative to the shaft when the support member is in the second position, and
    wherein the end of the support member engages a surface of the stopper when the support member is in the second position to prevent the support member from rotating relative to the shaft.

18. The surgical device recited in claim 16, wherein the support member is configured to translate relative to the sleeve when the support member is in the second position to increase a length of the balloon.

19. The surgical device recited in claim 16, wherein rotation of the shaft relative to the sleeve when the support member is in the second position causes the balloon to twist about the shaft.

20. A surgical device comprising:
- a sleeve;
- a shaft disposed in the sleeve, the shaft defining a passageway;
- a stopper disposed in the passageway;
- a balloon having a first end coupled to the sleeve and a second end coupled to the shaft, the balloon defining a chamber; and
- a support member disposed within the passageway and moveable relative to the shaft between a first position in which an end of the support member is spaced apart from the stopper and a second position in which the end of the support member is positioned within the stopper,
- wherein the shaft comprises an inner surface defining the passageway, the stopper having an outer surface that directly engages the inner surface, and
- wherein the stopper forms a plug that completely fills a portion of the passageway.

21. The surgical device recited in claim 19, wherein the support member is prevented from rotating relative to the shaft when the support member is in the second position.

* * * * *